United States Patent [19]

Akhavan-Tafti et al.

[11] Patent Number: 5,670,644
[45] Date of Patent: Sep. 23, 1997

[54] ACRIDAN COMPOUNDS

[75] Inventors: Hashem Akhavan-Tafti; Zahra Arghavani, both of Brighton; Renuka DeSilva, Northville, all of Mich.

[73] Assignee: Lumigen, Inc., Southfield, Mich.

[21] Appl. No.: 647,383

[22] Filed: May 9, 1996

Related U.S. Application Data

[63] Continuation-in-part of Ser. No. 300,462, Sep. 2, 1994, which is a continuation-in-part of Ser. No. 205,093, Mar. 2, 1994, which is a continuation-in-part of Ser. No. 228,290, Apr. 15, 1994, Pat. No. 5,523,212, which is a continuation-in-part of Ser. No. 61,810, May 17, 1993, Pat. No. 5,491,072.

[51] Int. Cl.$^6$ .................... C07D 285/38; C07D 295/00; G01N 33/533; G01N 33/532
[52] U.S. Cl. .................... 546/103; 436/546; 436/541; 436/501
[58] Field of Search ................................ 546/103

[56] References Cited

U.S. PATENT DOCUMENTS

| | | | |
|---|---|---|---|
| 4,950,613 | 8/1990 | Arnold et al. | 546/103 |
| 5,171,668 | 12/1992 | Sugiyama | 435/28 |
| 5,206,149 | 4/1993 | Oyama | 540/524 |
| 5,283,334 | 2/1994 | McCapra | 546/104 |
| 5,284,951 | 2/1994 | McCapra | 546/107 |
| 5,284,952 | 2/1994 | Ramakrishnan | 546/104 |

FOREIGN PATENT DOCUMENTS

| | | | |
|---|---|---|---|
| 9316195 | 8/1993 | WIPO | C12Q 1/28 |

OTHER PUBLICATIONS

McCapra, F., Accts. Chem. Res., 9(6), 201–8 (1976).
McCapra, F., et al., in Chemiluminescence and Bioluminescence, Plenum Press, NY, 1973, 313–323.
McCapra, F., Prog. Org. Chem., 8, 231–277 (1971).
McCapra, F., Pure Appl. Chem., 24, 611–629 (1970).
Kinkel, T., et al., J. Biolumin. Chemilumin., 4, 136–139 (1989).
Zomer, G., Stavenuiter, J.F.C., Anal. Chim. Acta, 227, 11–19 (1989).
Law, S.J., et al., J. Biolumin. Chemilumin., 4, 88–98 (1989).
Ii, M., et al., Biochem. Biophys. Res. Comm., 193(2), 540–5 (1993).
Thorpe, G., Kricka, L., in Bioluminescence and Chemilumin., New Persp., Scholmerich, 199–208 (1987).
Zomer, G., et al., in Luminescence Technipues in Chem. and Biochem. Anal., Baeyens, 505–521 (1991).
Stollé, R., J. Prakt. Chem., 105, 137–148 (1922).

*Primary Examiner*—Robert T. Bond
*Attorney, Agent, or Firm*—Richard S. Handley

[57] ABSTRACT

A chemiluminescent assay method, compositions, kits and chemiluminescent acridan compounds are described which use a two-step chemiluminescent reaction process. The reaction involves an acridan compound, preferably a derivative of an N-alkylacridan-9-carboxylic acid, which undergoes a reaction with a peroxide compound, a peroxidase enzyme and an enhancer under conditions of time, temperature and pH which permit the accumulation of an intermediate compound, which is subsequently induced to produce a burst of light by raising the pH. The result is generation of very high intensity light from the reaction. The peroxidase enzyme is present alone or linked to a member of a specific binding pair in an immunoassay, DNA probe assay or other assay where the hydrolytic enzyme is bound to a reporter molecule. The method is particularly amenable to automated assays because of the separation of the incubation and light generating steps.

12 Claims, 4 Drawing Sheets

ACRIDAN COMPOUNDS

CROSS REFERENCE TO RELATED APPLICATION

This application is a Continuation-In-Part of application Ser. No. 08/300,462 filed Sep. 2, 1994, which is a Continuation-In-Part of applicant's application Ser. Nos. 08/205,093 filed Mar. 2, 1994 and 08/228,290 filed Apr. 15, 1994, now U.S. Pat. No. 5,523,212, which are Continuations-In-Part of application Ser. No. 08/061,810 filed May 17, 1993, now U.S. Pat. No. 5,491,072.

BACKGROUND OF THE INVENTION

1. Field of the Invention

This invention relates to acridan compounds, particularly N-alkylacridancarboxylic acid derivatives which allow the production of light (chemiluminescence) by reaction with a peroxide and a peroxidase. This invention relates to stabilized chemiluminescent acridinium compounds, which are formed by the peroxidase-catalyzed oxidation of acridan compounds and whose chemiluminescent reaction with peroxide can be prevented until the desired time. This invention relates to an improved method of generating light chemically by the action of a peroxidase enzyme and an oxidant such as hydrogen peroxide with a group of N-alkylacridancarboxylic acid derivatives in which the enzymatic step and light producing step can be separated in time. The invention also relates to the use of specific enhancer substances for enhancing the amount of chemiluminescence produced from this method. The invention also relates to the use of this method to detect the hydrogen peroxide or peroxidase enzymes by a chemiluminescent assay. Further, the invention relates to the use of the method to detect and quantitate various biological molecules which can be directly or indirectly bound to a peroxidase enzyme. For example, the method may be used to detect haptens, antigens, proteins and antibodies by the technique of immunoassay, and DNA or RNA by nucleic acid hybridization assays. The method may additionally be used to detect enzymes which generate hydrogen peroxide such as oxidase and dehydrogenase enzymes or conjugates of such enzymes with biological molecules. The chemiluminescent methods of the invention are particularly useful for the detection of biological molecules in assays performed on automated instruments.

2. Description of Related Art

The detection and quantitation of biological molecules has been accomplished historically with excellent sensitivity by the use of radiolabeled reporter molecules. Recently numerous non-radioactive methods have been developed to avoid the hazards and inconvenience posed by these materials. Enzyme-linked detection techniques offer the best sensitivity since the catalytic turn over of substrate to produce a detectable change in effect amplifies the detected signal. Substrates which generate color, fluorescence or chemiluminescence have been developed, the latter achieving the best sensitivity.

Further increases in assay sensitivity will expand the range of utility of chemiluminescence-based methods by permitting the detection of analytes present in smaller quantities or reducing the amount of time and/or reagents required to perform the assay. A way to increase the speed and sensitivity of detection in a chemiluminescent assay is to cause the light to be emitted as a short pulse of high intensity.

Horseradish peroxidase (HRP) is one of the most extensively used enzymes in enzyme-linked detection methods such as immunoassays, detection of oligonucleotides and nucleic acid hybridization techniques. Chemiluminescent reagents for HRP detection known in the art do not fully utilize the beneficial properties of this enzyme in analysis mainly due to sensitivity limitations. More efficient chemiluminescent substrates are needed to improve the usefulness of this reporter enzyme. In addition, the ability to generate flashes of high intensity coupled with an enzymatic amplification step, which is unknown in the art, could provide additional benefits in detection sensitivity and automated detection.

a. Oxidation of Acridan

Applicants' U.S. Pat. No. 5,491,072 and co-pending applications, Ser. Nos. 08/205,093 filed Mar. 2, 1994 and 08/228,290 filed Apr. 15, 1994 the disclosures of which are incorporated herein by reference, disclose the use of a peroxidase enzyme to oxidize substituted and unsubstituted N-alkylacridan-carboxylic acid derivatives to generate chemiluminescence. In the presence of a peroxidase enzyme and a peroxide, N-alkylacridancarboxylic acid derivatives are efficiently oxidized to produce the N-alkylacridone and blue chemiluminescence in a one-step process.

Esters of 10-methylacridan-9-carboxylic acid undergo autoxidation to N-methylacridone in dipolar aprotic solvents under strongly basic conditions to produce chemiluminescence (F. McCapra, Acc. Chem. Res., 9(6), 201-8 (1976); F. McCapra, M. Roth, D. Hysert, K. A. Zaklika in *Chemiluminescence and Bioluminescence*, Plenum Press, New York, 1973, pp. 313–321; F. McCapra, *Prog. Org. Chem.*, 8, 231–277 (1971); F. McCapra, *Pure Appl. Chem.*, 24, 611–629 (1970); U.S. Pat. Nos. 5,283,334 and 5,284,951 to McCapra and 5,284,952 to Ramakrishnan). Chemiluminescence quantum yields ranged from $10^{-5}$ to 0.1 and were found to increase as the $pK_a$ of the phenol or alcohol leaving group decreased. Quantum yields in aqueous solution were significantly lower due a competing non-luminescent decomposition of an intermediate. Addition of the cationic surfactant CTAB increased the apparent light yield 130-fold by preventing a competing dark reaction.

b. Chemiluminescent Oxidation of Acridinium Esters

The chemiluminescent oxidation of aliphatic and aromatic esters of N-alkylacridinium carboxylic acid by $H_2O_2$ in alkaline solution is a well known reaction. The high chemiluminescence quantum yield approaching 0.1 has led to development of derivatives with pendant reactive groups for attachment to biological molecules. Numerous chemiluminescent immunoassays and oligonucleotide probe assays utilizing acridinium ester labels have been reported.

The use of acridinium esters (AE's), especially when labeled to a protein or oligonucleotide suffers from two disadvantages. The chief problem is limited hydrolytic stability. Acridinium ester conjugates decompose steadily at or slightly above room temperature by hydrolysis of the ester group. Depending on the substitution of the leaving group storage at −20° C. may be required for extended storage. Amides, thioesters and sulfonimides of N-alkylacridinium carboxylic also emit light when oxidized under these conditions (T. Kinkel, H. Lubbers, E. Schmidt, P. Molz, H. J. Skrzipczyk, *J. Biolumin. Chemilumin.*, 4, 136–139, (1989), G. Zomer, J. F. C. Stavenuiter, *Anal. Chim. Acta*, 227, 11–19 (1989)). These modified leaving groups only partially improve storage stability.

A second disadvantage of acridinium esters is the tendency to add nucleophiles such as water at the 9-position to form a non-luminescent pseudo-base intermediate which decomposes in a pH-dependent manner in a dark process. In practice, the pH of solutions containing acridinium esters must be first lowered to reverse pseudo-base formation and then raised in the presence of $H_2O_2$ to produce light.

A more fundamental limitation to the use of acridinium esters as chemiluminescent labels lies in the fact that when used as direct labels, only up to at most about 10 molecules can be attached to a protein or oligonucleotide. Coupled with the quantum efficiency for producing a photon ($\leq 10\%$), an acridinium ester-labeled analyte can generate at most one photon of light. In contrast, enzyme-labeled analytes detected by a chemiluminescent reaction can potentially generate several orders of magnitude more light per analyte molecule detected by virtue of the catalytic action of the enzyme.

An attempt to increase the number of acridinium ester molecules associated with an analyte in an immunoassay was made by constructing an antibody-liposome conjugate wherein the liposome contained an unspecified number of AE's (S.-J. Law, T. Miller, U. Piran, C. Klukas, S. Chang, J. Unger, *J. Biolumin. Chemilumin.*, 4, 88–98, (1989)). This method only produced a modest increase in signal over a comparable assay using directly labeled AE's.

c. Chemiluminescent Detection of Horseradish Peroxidase

Amino-substituted cyclic acylhydrazides such as luminol and isoluminol react with $H_2O_2$ and a peroxidase enzyme catalyst (such as horseradish peroxidase, HRP) under basic conditions with emission of light. This reaction has been used as the basis for analytical methods for the detection of $H_2O_2$ and for the peroxidase enzyme. An analog of luminol (8-amino-5-chloro-7-phenylpyrido[3,4-d]pyridazine-1,4 (2H,3H)dione) has been used in an enhanced chemiluminescent assay with HRP (M. Ii, H. Yoshida, Y. Aramaki, H. Masuya, T. Hada, M. Terada, M. Hatanaka, Y. Ichimori, Biochem. Biophys. Res. Comm., 193(2), 540-5 (1993)). Another chemiluminescent compound oxidized by a peroxidase enzyme and a peroxide is a hydroxy-substituted phthalhydrazide (Akhavan-Tafti co-pending U.S. patent application No. 965,231, filed Oct. 23, 1992). Applicant's co-pending application Ser. Nos. 08/061,810, 08/205,093 and 08/228,290 disclose chemiluminescent N-alkylacridancarboxylic acid esters, thioesters and sulfonimides which produce light upon reaction with a peroxide and a peroxidase for use in detecting peroxidase enzymes and in assays.

Numerous enhancers have also been employed in conjunction with the use of luminol to increase the intensity and duration of light emitted. These include benzothiazole derivatives such as D-luciferin, various phenolic compounds such as p-iodophenol and p-phenylphenol and aromatic amines (G. Thorpe, L. Kricka, in *Bioluminescence and Chemiluminescence, New Perspectives*, J. Scholmerich, et al, Eds., pp. 199–208 (1987)). For the purposes of the present-discussion phenolic compounds are taken to mean hydroxylic aromatic compounds which will also include compounds such as 2-naphthol and 6-bromo-2-naphthol which are known to enhance other peroxidase reactions in addition to the aforementioned substituted hydroxyphenyl compounds. Other compounds which function as enhancers of the chemiluminescent oxidation of amino-substituted cyclic acylhydrazides by a peroxidase are disclosed in U.S. Pat. No. 5,206,149 to Oyama and No. 5,171,668 to Sugiyama, PCT application WO 93/16195 dated Aug. 19, 1993 and in M. Ii, et al (infra).

OBJECTS

It is therefore an object of the present invention to provide an improved method and acridan compounds, especially aryl N-alkylacridancarboxylate derivatives with superior properties for use in generating chemiluminescence by the action of a peroxidase enzyme for the detection of biological materials and compounds. It is also an object of the present invention to provide an improved method and kit using aryl N-alkylacridancarboxylate derivatives for use in generating chemiluminescence by the action of a peroxidase enzyme for the detection of peroxidase enzymes and enzyme-conjugates in solution assays. Additionally, it is an object of the present invention to provide an improved method and kit using aryl N-alkylacridancarboxylate derivatives for use in generating chemiluminescence by the action of a peroxidase enzyme for use in nucleic acid assays in solution and on surfaces. Further, it is an object of the present invention to provide an improved method and kit using aryl N-alkylacridancarboxylate derivatives for use in generating chemiluminescence by the action of a peroxidase enzyme for detection of haptens, proteins and antibodies in enzyme immunoassays.

IN THE DRAWINGS

FIG. 1 is a graph showing the light emission profile from a reagent containing 2',3',6'-trifluorophenyl 1,6-dimethoxy-10-methylacridan-9-carboxylate (5c) of the present invention. Forty μL of a formulation was incubated with 1 μL of a solution containing $1.4 \times 10^{-16}$ mol of HRP in water. The formulation consisted of: 1.5 μM acridan compound 5c in 0.01M tris buffer, pH 8.0, 0.6 mM urea peroxide, 0.1 mM p-phenylphenol, 0.025% TWEEN 20, 1 mM EDTA. After 100 sec, 100 μL of 0.1M NaOH was injected. The figure shows the intense burst of light emission (in Relative Light Units, RLU) generated under these conditions.

FIG. 2 is a graph showing the linearity of detection of HRP using a reagent composition of the present invention. In separate experiments, 50 μL of a solution containing acridan 5c were mixed at room temperature with 1.25 μL aliquots of HRP containing the indicated amounts of enzyme. After 100 sec, 100 μL of 0.1M NaOH was injected. Light intensity was integrated for 2 sec. The term S-B refers to the chemiluminescence signal (S) in RLU in the presence of HRP corrected for background chemiluminescence (B) in the absence of HRP.

FIG. 3 is a graph showing a series of absorption spectra from reaction of the reagent of Example 11 containing acridan 5c (3 mL) with $1.1 \times 10^{-13}$ mol of HRP. The absorbance spectrum was scanned from 300–500 nm at 30 sec intervals after addition of enzyme. The progression of curves shows the formation (in the direction bottom curve to top curve at 400 nm) of the acridinium compound 4c with an isosbestic point at about 338 nm. After 15 min, no further change was observed in the spectrum.

FIG. 4 is a graph showing a series of absorption spectra from reaction of 3 mL of a reagent containing the acridan compound 2',6'-difluorophenyl 10-methylacridan-9-carboxylate with $1.1 \times 10^{-13}$ mol of HRP. The absorbance spectrum was scanned from 300–500 nm at 30 sec intervals after addition of enzyme. The progression of curves shows a more complex behavior with no isosbestic point indicating the formation (in the direction bottom curve to top curve at 400 nm) of both the acridinium compound 2',6'-difluorophenyl 10-methylacridinium-9-carboxylate and 10-methylacridone as proven by comparison with authentic samples of these two compounds.

DESCRIPTION OF THE PREFERRED EMBODIMENTS

Figure 1:
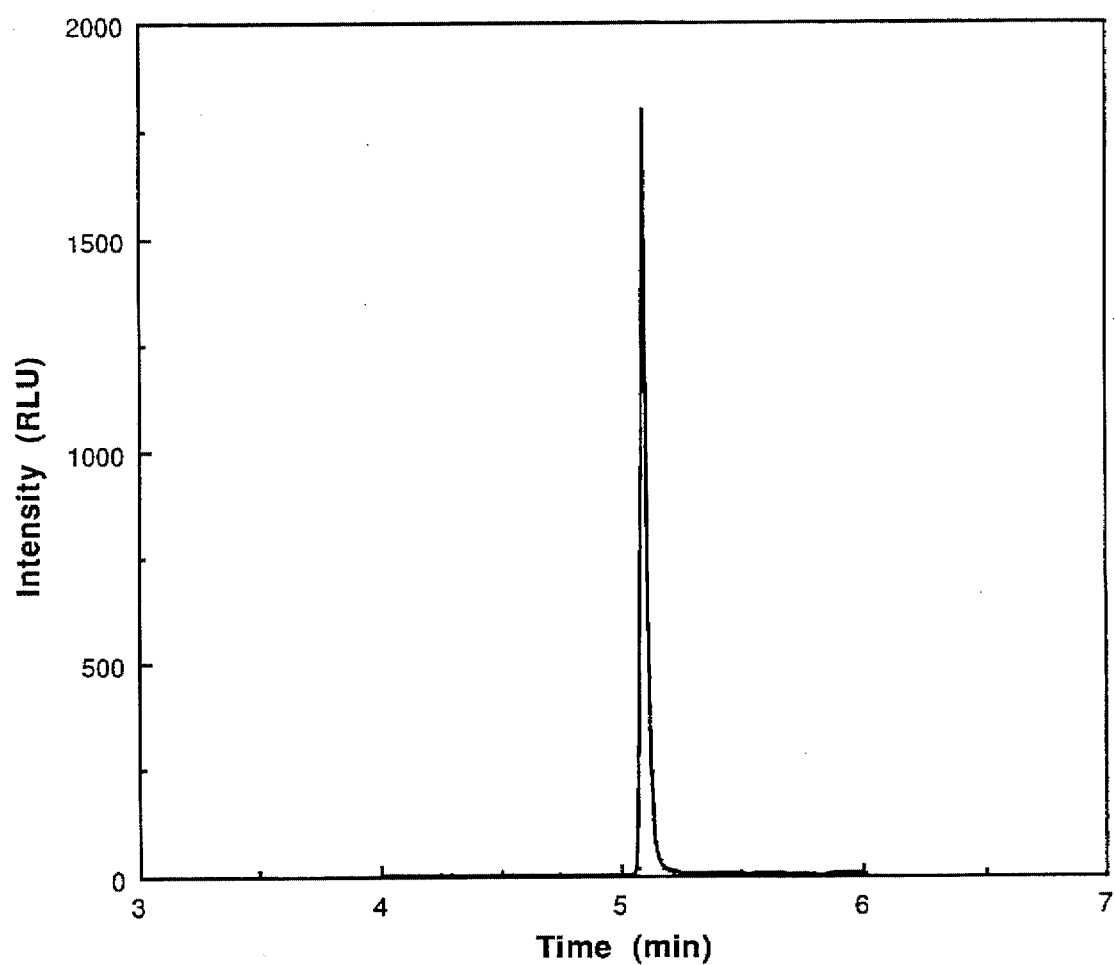

The present invention relates to a method for producing chemiluminescence which comprises:

a) reacting a peroxide compound and a peroxidase enzyme with an acridan under conditions of time, temperature and pH which permit the accumulation of an intermediate compound wherein the acridan has the formula:

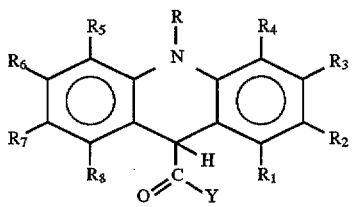     (I)

wherein R is selected from alkyl, heteroalkyl and aralkyl groups, wherein $R_1$ to $R_8$ are selected independently from groups which allow the production of light and wherein Y is a leaving group; and b) raising the pH to a level high enough to cause the production of a burst of light from reaction of the intermediate with peroxide at an intensity substantially greater than that being produced before raising the pH.

The present invention also relates to the use of this method for detecting an analyte selected from haptens, antigens, proteins and antibodies, DNA, RNA and oligonucleotides in an assay procedure by a chemiluminescent reaction, wherein the analyte is linked to or capable of being linked directly or indirectly to a peroxidase enzyme and wherein the amount of light produced is related to the amount of the analyte.

The present invention also relates to the use of this method for detecting a peroxidase enzyme in an assay procedure by a chemiluminescent reaction, wherein the amount of light produced is related to the amount of enzyme. The enzyme may be free, in which case it is the analyte, or linked to a member of a specific binding pair, for example, by using a biotin-labeled analyte and streptavidin-peroxidase conjugate. Other high affinity binding pairs well known in the art such as fluorescein and anti-fluorescein, digoxigenin and anti-digoxigenin or complementary nucleic acid sequences may also be readily employed as a means of linking a peroxidase enzyme to a member of a specific binding pair for the purpose of practicing this invention. The method may thus be used to detect haptens, antigens, proteins and antibodies by the technique of immunoassay and DNA or RNA by nucleic acid hybridization assays.

The present invention also relates to the use of this method for detecting hydrogen peroxide in an assay procedure by a chemiluminescent reaction with an acridan and a peroxidase enzyme, wherein the amount of light produced is related to the amount of the peroxide present. It will be apparent to those skilled in the art of chemiluminescent assays that the present methods can be used to detect oxidase enzymes and dehydrogenase enzymes. These enzymes can generate hydrogen peroxide through reduction of oxygen and oxidation of their native substrates. The hydrogen peroxide thereby produced can then be further reacted either concurrently as it is generated or in a subsequent step with an acridan compound of the present invention and a peroxidase to produce light. A property of the light produced is then related to the amount of the oxidase or dehydrogenase enzyme. Further the oxidase or dehydrogenase enzyme may be present as a conjugate to a biological molecule or a member of a specific binding pair in an assay for an analyte.

The present invention also contemplates kits for detecting any of an analyte, a peroxidase enzyme, a peroxidase enzyme conjugate, a peroxide or a reagent system or enzyme which produces hydrogen peroxide in an assay procedure by a chemiluminescent reaction. Kits useful for practicing the present invention in any of its embodiments will comprise in one or more containers:

a) an acridan compound as described above;

b) a reagent for raising the pH of the reaction solution;

c) a peroxide if the analyte to be detected is not the peroxide or a reagent which generates peroxide;

d) a peroxidase enzyme, if the analyte to be detected is not the peroxidase or a conjugate of a peroxidase with the analyte or a conjugate of a peroxidase with a reagent which forms a specific binding pair with the analyte.

In another aspect the present invention relates to particular acridan compounds of the formula:

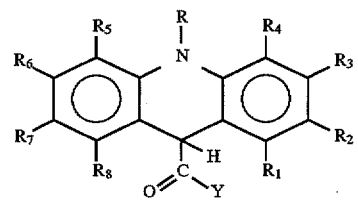

wherein R is selected from alkyl, heteroalkyl and aralkyl groups, wherein $R_1$ to $R_8$ are selected independently from groups which allow the production of light and wherein at least one of $R_1$ and $R_8$ is a group selected from alkyl, alkoxy and halogen groups and wherein Y is a leaving group which allows the production of light from the acridan by reaction with a peroxide and a peroxidase. The leaving group Y can be any group which allows the production of light including, without limitation, aryloxy such as phenoxy and naphthyloxy, alkylthio and arylthio, sulfonimide and other leaving groups known in the art.

Preferred groups of compounds are:

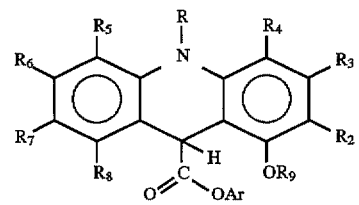

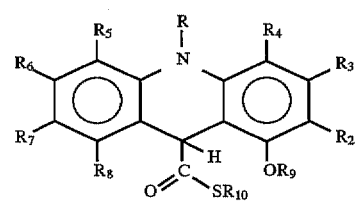

wherein R is an alkyl, aralkyl or heteroalkyl group, wherein $R_{2-8}$ are selected independently from groups which allow the light to be produced, wherein $OR_9$ is a $C_1$ to $C_{20}$ straight or branched chain alkoxy group, wherein Ar is substituted or unsubstituted aryl or heteroaryl and wherein $R_{10}$ is Ar or substituted or unsubstituted alkyl, aralkyl or heteroalkyl.

Another class of preferred compounds is:

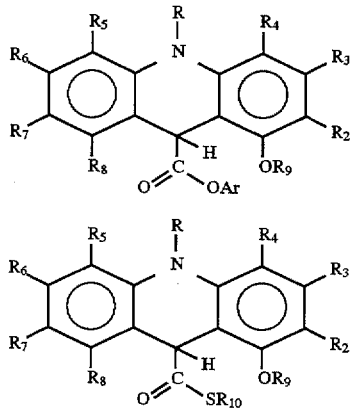

wherein at least one of $R_2$ through $R_8$ which may be the same or different are $C_1$ to $C_{20}$ straight or branched chain alkoxy groups and wherein $OR_9$, R, $R_{10}$ and Ar are as defined above.

Another class of preferred compounds is:

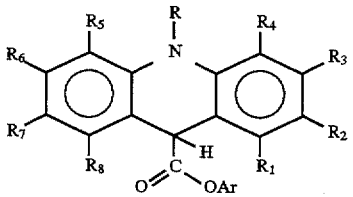

wherein R is an alkyl, aralkyl or heteroalkyl group, wherein $R_{2-8}$ are selected independently from groups which allow the light to be produced, wherein $R_1$ is selected from halogens and $C_1$ to $C_{20}$ straight or branched chain alkyl groups and wherein Ar is a substituted or unsubstituted aryl or heteroaryl group.

Acridan compounds useful in the practice of the present invention include, without limitation, those with Ar or $R_{10}$ groups consisting of substituted or unsubstituted aryl selected from phenyl, naphthyl, anthryl, phenanthryl and pyrenyl, heteroaryl selected from pyridyl, pyrimidinyl, pyridazinyl, quinolinyl, furyl, benzofuryl, thienyl, imidazolyl and the like. Groups which are contemplated as substituents include alkyl, alkenyl, alkynyl, aralkyl, aryl, alkoxyl, alkoxy-alkyl, hydroxyalkyl, halogen, carbonyl, carboxyl, carboxamide, cyano, trifluoromethyl, amino, trialkylammonium and nitro groups.

Modifications of the particular combinations of the groups R, $R_{10}$ and Ar can be readily made in order to optimize the properties of the acridan compound for particular applications without departing from the scope of the present invention. For example, substituents may be selected for ease of synthesis or to provide a compound with improved solubility or with particular reaction kinetics. Substituents may also be chosen to provide acridan compounds which have superior stability or diminish side reactions or improve chemiluminescence efficiency as will be appreciated by consideration of the reaction process detailed below and by reference to the examples.

The present invention involves improved acridan compounds which, upon reaction with a peroxidase enzyme and a peroxide compound, are converted into an intermediate acridinium compound, wherein the center ring is aromatic, which subsequently undergoes a rapid chemiluminescent reaction at higher pH. Conducting the chemiluminescent reaction in this manner results in a brief burst of light with a high peak intensity. In contrast, light generated by the method disclosed in U.S. Pat. No. 5,491,072 rises gradually over several minutes to a steady level. Reaction of the acridan with the peroxidase and peroxide will normally be carried out in an aqueous buffer solution at a pH which is compatible with enzyme activity, preferably between about 6 and about 8.5. The pH of the solution is then increased to above about 11 after a preliminary incubation period of a few seconds to several minutes. The intermediate formed by the enzymatic reaction produces a burst of luminescence by reaction with peroxide at the higher pH.

Scheme 1.

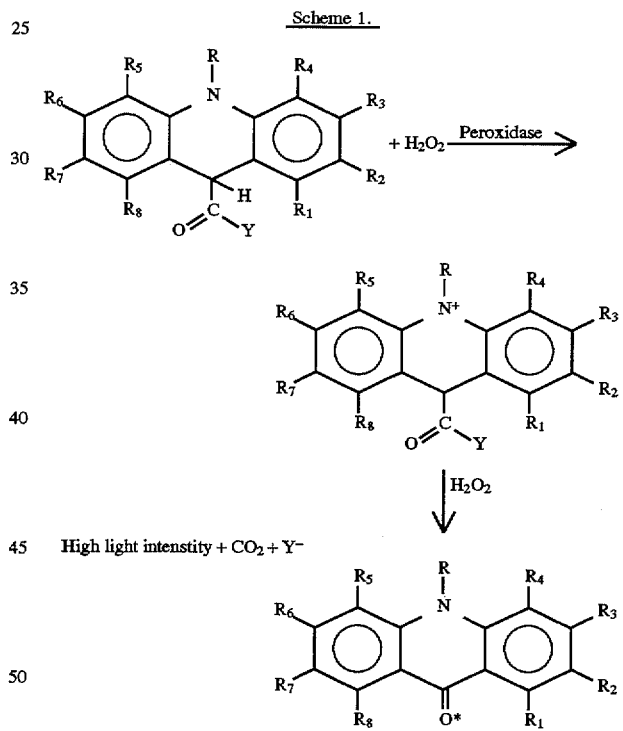

High light intenstity + $CO_2$ + $Y^-$

The rate of the chemiluminescent decomposition of the acridinium compound during the enzymatic oxidation phase can be slowed by appropriate choice of acridan compound or by adjusting reaction conditions allowing the acridinium compound to accumulate. The rate of autoxidation of the unreacted acridan compound can also be slowed by appropriate choice of ring substituents. For example, acridans with substituents other than hydrogen at the 1-position and acridans with two or more substituents selected from alkoxy, alkyl and halogen exhibit lower background (non-enzymatic) chemiluminescence and are oxidized to acridinium compounds with better stability. Subsequently making the reaction solution highly basic greatly accelerates the reaction of the acridinium with peroxide to expel the leaving group and $CO_2$ and produce light arising from the excited state of the N-substituted acridone.

Acridinium ester, thioester or sulfonimide compounds of the formula:

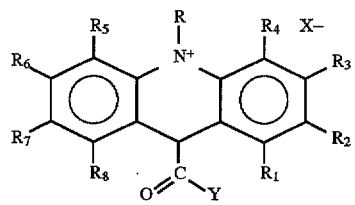

which are formed by the peroxidase-catalyzed oxidation of the corresponding acridan compound according to the present reaction are unexpectedly stable to peroxide under slightly acidic, neutral or moderately alkaline pH. Since the acridinium compound is formed in the presence of excess peroxide, any significant reactivity of the acridinium compound with the excess peroxide would lead to continuous light emission as the enzymatic reaction proceeds. Acridan compounds of the present invention produce acridinium compounds which are relatively unreactive to peroxide under the reaction conditions.

The chemiluminescent reaction of the present invention provides an unexpectedly sensitive method for detection of peroxidase enzymes or peroxide compounds. The analytical sensitivity as defined by the signal/background ratio is limited by the ability to distinguish the light produced by the base-induced reaction of the enzymatically produced intermediate from all other light producing processes. Quite unexpectedly, three potentially problematic side reactions do not take place to an extent that interferes with the measurement of the desired signal. First, the acridinium ester intermediates formed by enzymatic oxidation of the acridan in the present method produce relatively low levels of light at neutral to moderately alkaline pH. This is surprising in view of the fact that acridinium esters, thioesters and sulfonimides known in the art react rapidly with hydrogen peroxide to produce intense chemiluminescence.

Second, N-alkylacridancarboxylate esters themselves undergo a chemiluminescent reaction (autoxidation) with molecular oxygen at $pH \geq 11$ as discussed in McCapra, infra. Any unreacted acridan remaining after the incubation with enzyme would therefore be expected to produce a large background emission when the pH was raised. Surprisingly, the acridans of the present invention do not generate a significant quantity of light at the high pH used in the second step relative to the level of light produced from the enzymatically generated acridinium compound.

Third, acridinium compounds can undergo side reactions which do not produce light. Reactions well known in the art which consume the acridinium compound by competing non-luminescent pathways will decrease the amount of light which can be produced. Hydrolysis results in expulsion of the leaving group Y and formation of a non-luminescent carboxylate ion. Addition of nucleophiles to the 9-position results in an intermediate termed a pseudo-base. While this reaction is reversible by lowering the solution pH to about 1 to 3, this would unnecessarily complicate the reaction. Hydrolysis of the starting acridan as well would limit the amount of light which could be produced.

The reaction of the present invention is carried out in solution such as an aqueous buffer which may be in contact with the surface of a solid support such as a bead, tube, membrane or microwell plate coated with enzyme. Suitable buffers include any of the commonly used buffers capable of maintaining a pH in the range of about 6 to about 8.5 for example, phosphate, borate, carbonate, tris (hydroxymethylamino)methane, glycine, tricine, 2-amino-2-methyl-1-propanol, diethanolamine and the like. The preferred method of practicing the invention in this regard is determined by the requirements of the particular intended use.

Incorporation of certain enhancer compounds either alone or in combination with surfactants into the reaction mixture promotes the reactivity of the enzyme. Since the enzymatically produced intermediate undergoes a subsequent chemiluminescent reaction upon raising the pH, the enhanced production of intermediate translates to enhanced production of light. Included among these enhancers are phenolic compounds and aromatic amines known to enhance other peroxidase reactions as described in G. Thorpe, L. Kricka, in *Bioluminescence and Chemiluminescence, New Perspectives*, J. Scholmerich, et al, Eds., pp. 199–208 (1987), M. Ii, H. Yoshida, Y. Aramaki, H. Masuya, T. Hada, M. Terada, M. Hatanaka, Y. Ichimori, *Biochem. Biophys. Res. Comm.*, 193(2), 540-5 (1993), and in U.S. Pat. Nos. 5,171,668 and 5,206,149 which are incorporated herein by reference. Substituted and unsubstituted arylboronic acid compounds and their ester and anhydride derivatives as disclosed in PCT WO 93/16195, Aug. 19, 1993 and incorporated herein by reference are also considered to be within the scope of enhancers useful in the present invention. Preferred enhancers include but are not limited to: p-phenylphenol, p-iodophenol, p-bromophenol, p-hydroxycinnamic acid, 2-naphthol and 6-bromo-2-naphthol.

Additives which suppress the generation of chemiluminescence from the reaction of hydrogen peroxide and aryl acridan derivatives in the absence of peroxidase enzymes are employed to further improve the utility of the invention. It has also been found that certain surfactants such as anionic, cationic and nonionic surfactants improve the sensitivity of detection of the peroxidase enzyme in assays of the present invention by providing a larger signal.

The preferred amounts of the various components of a composition of the present invention are shown in Table I.

TABLE I

| | |
|---|---|
| Acridan | 1 nM–1 mM |
| Phenol enhancer | 1 μm–10 mM |
| Surfactant | 0.005–5% |
| Peroxide | 0.01–10 mM |
| Chelating agent | 0.01–5 mM |

The present invention involves a solution in an aqueous buffer containing 1) a phenol enhancer or a salt of a phenol enhancer, 2) a peroxide compound wherein the peroxide compound may be, without limitation, hydrogen peroxide, urea peroxide, or a perborate salt, 3) an acridan compound of the invention, 4) a polydentate cation complexing agent such as EDTA, EGTA and their salts, and 5) a surfactant such as the anionic surfactant sodium dodecyl sulfate (SDS), or preferably a nonionic surfactant such as polyoxyethylenated alkylphenols, polyoxyethylenated alcohols, polyoxyethylenated ethers, polyoxyethylenated sorbitol esters and the like.

In a preferred method of practicing the present invention, an aqueous buffer solution with a pH in the range of about 5 to about 9 containing a phenol compound such as p-phenylphenol or p-iodophenol at a final concentration from about 0.01M to $1\times10^{-6}$M, a nonionic surfactant at a final concentration from about 5% to 0.005% (v/v), a peroxide source such as hydrogen peroxide or, preferably, a perborate salt or urea peroxide and a cation complexing agent such as EDTA at a final concentration from about $1\times10^{-3}$M to $1\times10^{-5}$M is mixed with a second solution containing an acridan compound of the invention to achieve a final acridan concentration from about 0.001M to about $1\times10^{-9}$M to form the detection reagent solution. This solution is contacted with the peroxidase enzyme which may either be in solution or adhered to a solid support. The detection reaction may be performed over a range of temperatures including at least the range 10°–40° C. After an incubation period, the pH of the solution is raised to at least about 10 by addition of a base and, optionally, additional peroxide. As a result, light is produced which rapidly rises to a maximum level and decays. Preferably the addition of base is done rapidly so that the light is emitted over a time interval of a few seconds. Adjustments of incubation time and temperatures and reaction pH as are apparent to the skilled artisan are considered to be within the subject matter of the invention.

A significant advantage of aryl acridan derivatives and compositions of the present invention containing them includes the ability to measure all of the light emitted from the accumulated chemiluminescent product in a short period of time. Measurement of the total light emission which occurs within a period of a few seconds is equivalent to integrating the intensity vs. time curve produced by reaction of applicant's previously disclosed acridans which produce an extended emission. As a result of the time compression of light emission, very small amounts of peroxidase enzyme activity yield large, easily measured spikes of light. This can lead to improved sensitivity of detection if background chemiluminescence is controlled. Assays designed with this type of light detection are readily adapted to existing high volume commercial immunoassay instruments. These and other advantages will be apparent by consideration of the examples.

EXAMPLES

Synthesis of Acridan Derivatives

Acridancarboxylic acid derivatives 5a–h were synthesized according to one of the methods shown in Scheme 2 from the corresponding acridine-9-carboxylic acid. In the structure shown below, the identity and position of substituents A and B are explained in the table. All other substituents are H.

TABLE II

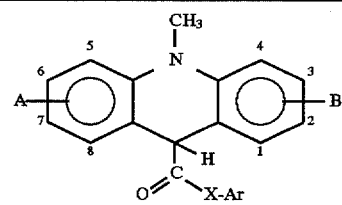

| Compound | A | B | X | Ar |
|---|---|---|---|---|
| 5a | 3-OCH₃ 4-Cl | H | O | 2',3',6'-Trifluorophenyl |
| 5b | 3-OCH₃ 4-Cl | H | S | 4'-Fluorophenyl |
| 5c | 1-OCH₃ | 6-OCH₃ | O | 2',3',6'-Trifluorophenyl |
| 5d | OCH₃ Cl | OCH₃ Cl | O | 2',3',6'-Trifluorophenyl |
| 5e | 3-OCH₃ | 6-OCH₃ | O | 2',3',6'-Trifluorophenyl |
| 5g | 1-CH₃ | H | O | 2',3',6'-Trifluorophenyl |
| 5h | 1-Cl | H | O | 2',3',6'-Trifluorophenyl |
| 5i | 1-OCH₃ 4-CH₃ | 6-OCH₃ | O | 2',3',6'-Trifluorophenyl |
| 5j | 1-CH₃ 4-CH₃ | H | O | 2',3',6'-Trifluorophenyl |
| 5k | 1-OCH₃ 4-OCH₃ | H | O | 2',3',6'-Trifluorophenyl |

The structure of compound 5d has not been completely determined since the position of the OCH₃ and Cl substituents is not known with certainty. The simplicity of the ¹H NMR spectrum indicates a high degree of symmetry.

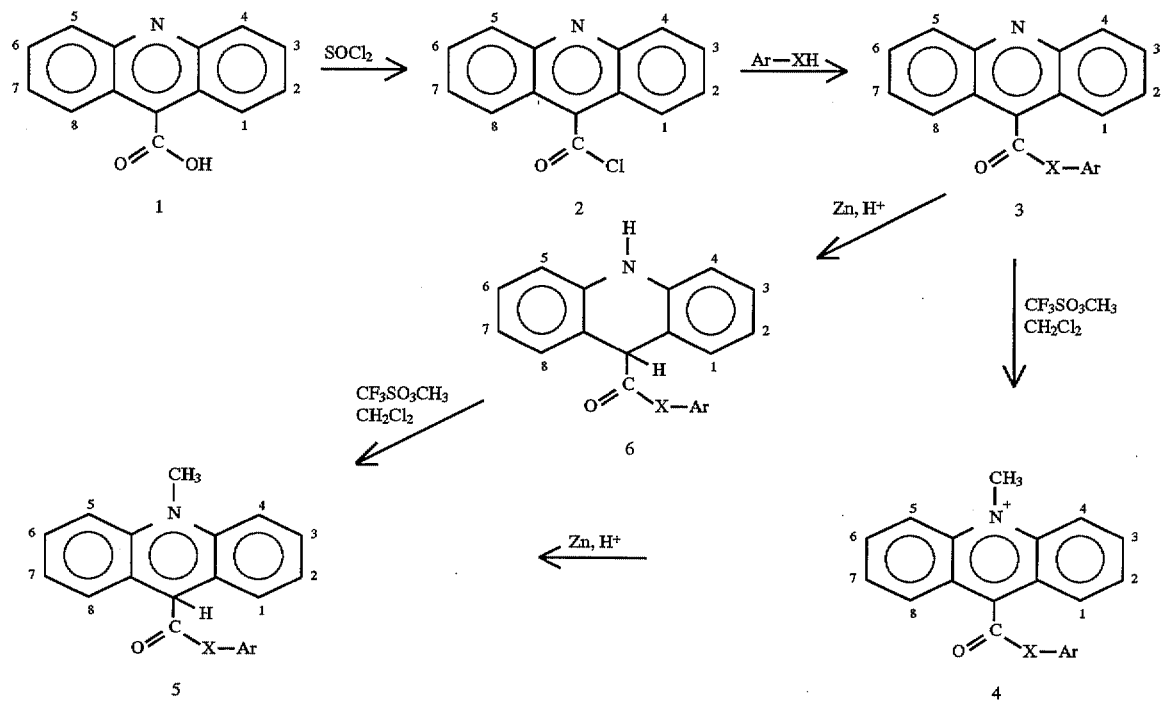

Scheme 2. Preparation of Acridan Compounds

The acridine-9-carboxylic acid compounds 1c, e, f, g and h were prepared by literature methods (G. Zomer, J. Stavenuiter, R. Van Den Berg, E. Jansen, In *Luminescence Techniques in Chemical and Biochemical Analysis*, W. Baeyens, D. De Keukeleire, K. Korkidis, eds., Dekker, New York, 505–521, (1991); R. Stollé, *J. Prakt. Chem.*, 105, 137, (1922)). The acid chloride 2a (A=3—OCH$_3$, 4-Cl; B=H) was produced during the reaction of 1f with SOCl$_2$ in addition to 2f.

TABLE III

| Compound | A | B |
|---|---|---|
| 1c | 1-OCH$_3$ | 6-OCH$_3$ |
| 1e | 3-OCH$_3$ | 6-OCH$_3$ |
| 1f | 3-OCH$_3$ | H |
| 1g | 1-CH$_3$ | H |
| 1h | 1-Cl | H |
| 1i | 1-OCH$_3$  4-CH$_3$ | 6-OCH$_3$ |
| 1j | 1-CH$_3$  4-CH$_3$ | H |
| 1k | 1-OCH$_3$  4-OCH$_3$ | H |

Example 1

Synthesis of Compound 5a

2',3',6'-Trifluorophenyl 4-chloro-3-methoxy-10-methylacridan-9-carboxylate.

(a) Condensation of the commercially available (Aldrich) 3-methoxydiphenylamine with oxalyl chloride produced 3-methoxyacridinecarboxylic acid (1f) which was used to prepare acid chloride 2a.

(b) Compound 1f was converted to a mixture of compounds 2a and 2f (1.5 g) by refluxing in 10 mL of SOCl$_2$ for 3 h. The solvent was removed under reduced pressure to obtain a yellow solid which was dissolved in methylene chloride (CH$_2$Cl$_2$) and pyridine (0.7 mL) under argon. A solution of the phenol (0.878 g) in CH$_2$Cl$_2$ was added dropwise. The solution was stirred overnight at room temperature then diluted with more CH$_2$Cl$_2$ (100 mL) and washed with water (3×50 mL). The organic layer was dried over Na$_2$SO$_4$ and concentrated to obtain a mixture of esters 3a and 3f. The product 2',3',6'-trifluorophenyl 4-chloro-3-methoxyacridine-9-carboxylate (3a) was isolated by chromatography on silica with 25% ethyl acetate/hexane: $^1$H NMR (CDCl$_3$) δ 4.15 (s, 3H), 7.1 (m, 1H), 7.2 (m, 1H), 7.59 (d, 1H), 7.65 (ddd, 1H), 7.85 (ddd, 1H), 8.17 (dt, 2H), 8.39 (dt, 1H); $^{13}$C NMR (CDCl$_3$) δ 57, 110.0, 114.7, 116.7, 117.2, 118.9, 121.3, 124.5, 124.6, 127.6, 127.8, 130.3, 131.2, 134.9, 144.2, 145.5, 148.5, 149.3, 150.0, 156.0, 163.7. The structure of this compound was verified by $^1$H-$^{13}$C NOE experiments, a $^1$H-coupled $^{13}$C NMR spectrum and a $^1$H-$^{13}$C 2D NMR spectrum which established the position of substitution of the OCH$_3$ and Cl groups and mass spectrometry. MS (m/z) 417, 270 (100), 242, 164.

(c) Ester 3a (0.223 g) was dissolved in 70 mL of ethanol with heating under an atmosphere of argon. After cooling to room temperature and shielding the flask from light, 0.313 g of NH$_4$Cl (10 eq.) was added followed by 0.382 g (10 eq.) of zinc dust. After 90 min, the solids were filtered off, washed with CH$_2$Cl$_2$ and the combined solvents evaporated. The resulting solid material was dissolved in CH$_2$Cl$_2$ and filtered yielding a light yellow material identified as 2',3',6'-trifluorophenyl 4-chloro-3 -methoxyacridan-9-carboxylate (6a) by TLC which showed the material to be pure and have an R$_f$ different from the starting ester.

(d) The reduced product was methylated with methyl triflate (7 mL) in ca. 8 mL of $CH_2Cl_2$ under argon with protection from light. After 4 days the volatiles were evaporated and the product chromatographically purified on silica using 50% ethyl acetate/hexane yielding compound 5a as a white solid.

Example 2

Synthesis of Compound 5b

4'-Fluorophenyl 4-chloro-3-methoxy-10-methylacridan-9-thiocarboxylate.

(a) Acid 1f was converted to the acid chlorides 2a and 2f as described in Example 1. The mixture of products 2a and 2f was dissolved in ca. 200 mL of $CH_2Cl_2$ under argon. Pyridine (4.2 mL, 1.3 eq.) was added and the solution stirred for 15 min. 4-Fluorothiophenol (5.4 mL, 1.2 eq.) was added and the warm solution stirred over night. Additional $CH_2Cl_2$ (100 mL) was added and the solution extracted with water and saturated NaCl. The organic layer was dried over $Na_2SO_4$ and concentrated to a brown solid. The product 4'-fluorophenyl 4-chloro-3-methoxyacridine-9-thiocarboxylate (3b) was isolated by chromatography on silica with solvents of graded polarity ranging from 20% ethyl acetate/hexane to pure ethyl acetate: $^1H$ NMR ($CDCl_3$) δ 4.162 (s, 3H), 7.18–7.24 (m, 2H), 7.55–7.65 (m, 4H), 7.82–7.88 (m, 1H), 8.07–8.10 (d, 2H), 8.35–8.38 (d, 1H).

(b) Thioester 3b (1.19 g) was dissolved in 300 mL of ethanol with heating. After cooling to room temperature and shielding the flask from light, 1.75 g of $NH_4Cl$ (10 eq.) was added followed by 2.14 g (10 eq.) of zinc dust. After 15 min, the solids were filtered off, washed with $CH_2Cl_2$ and the combined solvents evaporated. The resulting solid material was dissolved in $CH_2Cl_2$ and filtered yielding a light brown material identified as 4'-fluorophenyl 1-methoxyacridan-9-thiocarboxylate (6b) by $^1H$ NMR which was used with no additional purification for preparation of compound 5b: $^1H$ NMR ($CDCl_3$) δ 3.928 (s, 3H), 5.165 (s, 1H), 6.56–6.59 (d, 1H), 6.89–7.03 (m, 5H), 7.16–7.34 (m, 4H).

(c) The reduced product was methylated with methyl triflate (12 mL) in 5 mL of $CH_2Cl_2$ under argon with protection from light. After 72 hours the volatiles were evaporated and the product chromatographically purified on silica using 10–20% ethyl acetate/hexane yielding 0.75 g of 5b as a white solid: $^1H$ NMR ($CDCl_3$) δ 3.712 (s), 3.916 (s, 3H), 4.892 (s, 1H), 6.66–6.69 (d, 1H), 6.97–7.06 (m, 3H), 7.12–7.27 (m, 5H), 7.31–7.37 (m, 1H).

Example 3

Synthesis of Compound 5c

2',3',6'-Trifluorophenyl 1,6-dimethoxy-10-methylacridan-9-carboxylate.

(a) Reaction of bis(3-methoxyphenyl)amine (Aldrich) with $AlCl_3$ and oxalyl chloride followed by base-catalyzed rearrangement of the isatins produced a mixture of carboxylic acids. The mixed acids (1.4 g, 4.9 mmol) were suspended in excess $SOCl_2$ (15 mL) and the reaction mixture was refluxed for 4 h. The solvent was removed under reduced pressure and the acid chloride product was combined with 2,3,6-trifluorophenol (0.74 g, 5 mmol) and $CH_2Cl_2$. Pyridine (1 mL, 13 mmol) was added dropwise under argon. The solution was stirred overnight at room temperature and the volatiles removed under reduced pressure. The crude product was subjected to column chromatography on silica using 10% ethyl acetate/hexane. Pure 2',3',6'-trifluoro-phenyl 1,6-dimethoxyacridine-9-carboxylate (3c) was thereby isolated from the mixture of ester products along with two other esters designated 3d, whose structure is not precisely known, and 3e. Compound 3c: $^1H$ NMR ($CDCl_3$) δ 4.03 (s, 3H), 4.04 (s, 3H), 6.85–6.88 (d, 1H), 7.02–7.24 (m, 2H), 7.32–7.36 (dd, 1H), 7.48–7.49 (d, 1H), 7.70–7.83 (m, 2H), 8.08–8.11 (d, 1H).

(b) Ester (3c) (0.2 g, 0.46 mmol) was methylated by overnight stirring in 10 mL of $CH_2Cl_2$ with methyl trifluoromethanesulfonate (1 mL, 8.8 mmol) under argon. Volatiles were evaporated under reduced pressure and the residue washed with ethyl acetate. N-Methylacridinium ester (4c) was used directly in the next step.

(c) Reduction to the acridan (5c) was accomplished by reacting a solution of 4c (45 mg) and 1 g of $NH_4Cl$ in 25 mL of ethanol with 1 g of zinc. The yellow solution decolorized immediately and was stirred an additional 30 min. Ethyl acetate (50 mL) was added and the mixture filtered. Evaporation of solvents and chromatography of the residue on silica with 10% ethyl acetate/hexane produced pure 5c: $^1H$ NMR ($CDCl_3$) δ 3.39 (s, 3H), 3.84 (S, 3H), 3.90 (S, 3H), 5.90 (s, 1H), 6.50–7.43 (m, 8H).

Example 4

Synthesis of Compound 5d

2',3',6'-Trifluorophenyl dichlorodimethoxy-10-methylacridan-9-carboxylate.

(a) Ester 3d was isolated by chromatography from the experiment described in Example 3. $^1H$ NMR ($CDCl_3$) δ 4.17 (s, 6H), 7.10–7.30 (m, 2H), 7.58–7.61 (d, 2H), 8.16–8.19 (d, 2H). Substitution of two chlorine atoms on the acridine ring was shown by mass spectrometry. MS (m/z) 481, 334 (100), 306. The substitution pattern of this product has not been determined unambiguously although the simplicity of the 1H NMR spectrum indicates that the compound is symmetrical.

(b) To a warm solution of ester (0.02 g) and ammonium chloride (2 g) in ethanol (25 ml) was added zinc (2 g) causing immediate decolorization of the solution. The colorless solution was stirred at room temperature for 30 min. Ethyl acetate (200 mL) was added to the solution which was then filtered. The solvents were removed from the filtrate under reduced pressure. The crude material obtained was chromatographed on silica gel (10% ethyl acetate/hexane) to yield the pure product (6d). $^1H$ NMR (acetone-$d_6$) δ 3.99 (s, 6H), 5.66 (s, 1H), 6.87–6.89 (d, 2H), 7.12–7.40 (m, 2H), 7.43–7.46 (d, 2H), 7.58 (s, 1H).

(c) The reduced product (0.16 g, 0.46 mmol) was methylated with methyl triflate (3 mL) in 5 mL of $CH_2Cl_2$ under argon with protection from light. After 72 hours the volatiles were evaporated and the product chromatographically purified on silica using 30% ethyl acetate/hexane yielding 5d as a white solid: $^1H$ NMR ($CDCl_3$) δ 3.47 (s, 3H), 3.91 (s, 3H), 5.03 (s, 1H), 6.74–6.77 (d, 2H), 7.80–7.00 (m, 2H), 7.21–7.23 (d, 2H). As indicated above for 3d, the substitution pattern of this product has not been determined unambiguously although the simplicity of the $^1H$ NMR spectrum indicates that the compound is symmetrical.

Example 5

Synthesis of Compound 5e

2',3',6'-Trifluorophenyl 3,6-dimethoxy-10-methylacridan-9-carboxylate.

(a) Ester 3e was isolated by chromatography from the experiment described in Example 3. $^1H$ NMR ($CDCl_3$) δ

4.03 (s, 6H), 7.11–7.24 (m, 2H), 7.29–7.33 (dd, 2H), 7.47–7.48 (d, 2H), 8.08–8.11 (d, 2H).

(b) Ester 3e (1 g, 2.3 retool) was methylated by overnight stirring in 30 mL of $CH_2Cl_2$ with methyl triflate (1.3 mL, 5 eq.) under argon. Volatiles were evaporated under reduced pressure and the residue washed with ethyl acetate. N-Methylacridinium ester (4e) was used directly in the next step. $^1H$ NMR (DMSO-$d_6$) δ 4.25 (s, 6H), 4.73 (s, 3H), 7.60–8.23 (m, 8H).

(c) Reduction to acridan 5e was accomplished by reacting a solution of 4e (650 mg) and 650 mg of $NH_4Cl$ in 100 mL of ethanol with 650 mg of zinc. The yellow solution decolorized immediately and was stirred an additional 30 min. Ethyl acetate (150 mL) was added and the mixture filtered. Evaporation of solvents and chromatography of the residue on silica with 10% ethyl acetate/hexane produces pure 5e. $^1H$ NMR (acetone-$d_6$) δ 3.48 (s, 3H), 3.88 (s, 6H), 5.41 (s, 1H), 6.62–7.39 (m, 8H).

Example 6

Synthesis of Compound 5g

2',3',6'-Trifluorophenyl 1,10-dimethylacridan-9-carboxylate.

(a) Reaction of 3-methyldiphenylamine (Aldrich) with $AlCl_3$ and oxalyl chloride followed by base-catalyzed rearrangement of the isatins produced a mixture of 1-methylacridine-9-carboxylic acid and 3-methylacridine-9-carboxylic acid. The mixed acids (4 g, 15.6 mmol) were suspended in excess $SOCl_2$ (50 mL) and the reaction mixture was refluxed for 1.5 h. The solvent was removed under reduced pressure. To the above residue was added 2,3,6-trifluorophenol (2.77 g, 18.7 mmol). This mixture was dissolved in $CH_2Cl_2$ and pyridine (4 ml, 49.5 mmol) was added dropwise under argon. The solution was stirred for several days at room temperature, then the solvent and excess pyridine were removed under reduced pressure. The crude material obtained was chromatographed on silica gel (5% ethyl acetate/hexane) to yield 1-methylacridan ester 3 g and the isomeric 3-methyl ester. Compound 3 g: $^1H$ NMR (CDCl$_3$) δ 7.04–7.25 (m, 2H), 7.70–7.77 (m, 3H), 7.87–7.92 (t, 1H), 8.24–8.31 (m, 3H).

(b) Ester 3g (0.2 g) and ammonium chloride (2 g) in ethanol (200 ml) are treated with zinc (2 g) causing immediate decolorization of the solution. The colorless solution is stirred at room temperature for 30 min. Ethyl acetate (200 mL) is added to the solution which is then filtered. The solvents are removed from the filtrate under reduced pressure. The crude material is chromatographed on silica gel (40% ethyl acetate/hexane) to yield 2',3',6'-trifluorophenyl 1-methylacridan-9-carboxylate (6 g).

(c) The reduced product (0.18 g) is methylated with methyl triflate (3 mL) in 5 mL of $CH_2Cl_2$ under argon with protection from light. After about 72 hours the volatiles are evaporated and the product chromatographically purified on silica using 30% ethyl acetate/hexane to yield 5 g as a white solid.

Example 7

Synthesis of Compound 5h

2',3',6'-Trifluorophenyl 1-chloro-10-methylacridan-9-carboxylate.

(a) Reaction of 3-chlorodiphenylamine (Aldrich) with $AlCl_3$ and oxalyl chloride followed by base-catalyzed rearrangement of the isatins produced a mixture of 1-chloroacridine-9-carboxylic acid and 3-chloroacridine-9-carboxylic acid. The mixed acids (4.0 g, 15.6 mmol) were suspended in excess $SOCl_2$ (50 mL) and the reaction mixture was refluxed for 1.5 h. The solvent was removed under reduced pressure. To the above residue was added 2,3,6-trifluorophenol (2.77 g, 18.7 mmol). This mixture was dissolved in $CH_2Cl_2$ and pyridine (4 ml, 49.5 mmol) was added dropwise under argon. The solution was stirred for several days at room temperature, then the solvent and excess pyridine were removed under reduced pressure. The crude material obtained was chromatographed on silica gel (5% ethyl acetate/hexane) to yield 1-chloroacridine ester 3 h and the isomeric 3-chloro ester.

Compound 3h: $^1H$ NMR (CDCl$_3$) δ 7.04–7.25 (m, 2H), 7.70–7.77 (m, 3H), 7.87–7.92 (m, 1H), 8.24–8.31 (m, 3H).

(b) To a warm solution of ester 3 h (0.2 g, 0.52 mmol) and ammonium chloride (2 g) in ethanol (200 ml) was added zinc (2 g) causing immediate decolorization of the solution. The colorless solution was stirred at room temperature for 30 min. Ethyl acetate (200 mL) was added to the solution which was then filtered. The solvents were removed from the filtrate under reduced pressure. The crude material obtained was chromatographed on silica gel (40% ethyl acetate/hexane) to yield the pure product 2,3,6-trifluorophenyl 1-chloroacridan-9-carboxylate (6 h). $^1H$ NMR (CDCl$_3$) δ 5.72 (s), 6.29 (s), 6.68–6.70 (d), 6.77–6.79 (d), 6.79–6.88 (m), 6.96–7.03 (m), 7.12–7.17 (t), 7.21–7.27 (d), 7.54–7.76 (d).

(c) The reduced product 6 h (0.18 g, 0.46 mmol) was methylated with methyl triflate (3 mL) in 5 mL of $CH_2Cl_2$ under argon with protection from light. After 72 hours the volatiles were evaporated and the product chromatographically purified on silica using 30% ethyl acetate/hexane yielding 5 h as a white solid: $^1H$ NMR (CDCl$_3$) δ 3.441 (S, 3H), 5.754 (s, 1H), 6.81–7.09 (m, 6H), 7.22–7.38 (m, 2H), 7.52–7.55 (dd, 1H).

Example 8

Synthesis of Compound 5i

2',3',6'-Trifluorophenyl 1,6-dimethoxy-4,10-dimethylacridan-9-carboxylate.

(a) 5-Methoxy-2-methylaniline (9.77 g, Aldrich) was converted to the acetamide derivative by reaction with 8.7 mL of acetic anhydride, 8.2 mL of acetic acid and 43 mg of zinc at reflux for 7 h. The reaction mixture was poured into 250 mL of ice water and stirred. The light brown solid was filtered and air-dried yielding 6.37 g of the product: $^1H$ NMR (CDCl$_3$) δ 1.579 (s,3H), 2.196 (s,3H), 3.791 (s,3H), 6.62–6.66 (dd, 1H), 6.92 (m, 1H), 7.06–7.08 (d, 1H), 7.554 (s, 1H).

(b) 5-Methoxy-2-methylacetanilide (6.37 g) was condensed with 3-bromoanisole (11.1 mL) in the presence of 5.06 g of $K_2CO_3$ and 0.74 g of CuI at reflux for 8 h. After standing overnight, the mixture was heated and then extracted with toluene (3×100 mL) and evaporated to a brown oil.

The oil was dissolved in 150 mL of ethanol, 4 g of KOH were added and the mixture refluxed for 9 h. The ethanol was evaporated and the red-brown solid taken up in 300 mL of water and extracted with ethyl acetate. The ethyl acetate was evaporated and the crude solid partially purified by passing a $CH_2Cl_2$ solution through a plug of silica. Final purification was effected by column chromatography on silica (5% ethyl acetate/hexane) to produce 7.63 g of the diphenylamine compound: $^1$H NMR (CDCl$_3$) δ 2.194 (s,3H), 3.752 (s, 3H), 3.783 (s,3H), 5.404 (s, 1H), 6.47–6.52 (m, 2H), 6.55–6.62 (m, 2H), 6.85–6.86 (d, 1H), 7.08–7.10 (d, 1H), 7.14–7.20 (t, 1H).

(c) Reaction of 5-methoxy-2-methylphenyl-3'-methoxyphenylamine (7.63 g) with 3.12 mL of oxalyl chloride in 110 mL of CH$_2$Cl$_2$ and followed by reaction with 8.36 g of AlCl$_3$ produced the isatin which was converted by base-catalyzed rearrangement with 100 mL of 10% KOH and neutralization to 1,6-dimethoxy-4-methylacridine-9-carboxylic acid (1i), (8.75 g): $^1$H NMR (CD$_3$OH/KOH) δ 2.168 (s, 3H), 3.706 (s, 3H), 3.763 (s, 3H), 6.30–6.34 (m, 2H), 6.70–6.74 (dd, 1H), 6.88–6.89 (d, 1H), 7.184–7.213 (d, 1H), 7.693–7.721 (d, 1H).

(d) Acid 1i (1.0 g) was dissolved in pyridine (20 mL). p-Toluenesulfonyl chloride (1.28 g) was added and the reaction mixture was stirred for 1 h. 2,3,6-Trifluorophenol (1.0 g) in 5 mL of pyridine was added and the solution was stirred overnight at room temperature. The ester product was isolated by chromatography on silica gel (20–40% ethyl acetate/hexane). A second chromatogratphic purification using 50% CH$_2$Cl$_2$/hexane yielded 110 mg of ester 3i: $^1$H NMR (CDCl$_3$) δ 2.841 (s, 3H), 4.003 (s, 3H), 4.051 (s, 3H), 6.75–6.78 (d, 1H), 7.04–7.23 (m, 2H), 7.31–7.36 (dd, 1H), 7.53–7.57 (m, 2H), 8.08–8.11 (d, 1H). Attempted preparation of the ester by making the acid chloride with SOCl$_2$ resulted in chlorination of the acridine ring.

(e) To a slurry of ester 3i (110 mg) and NH$_4$Cl (138 mg) in Ar-purged 2-propanol (25 mL) was added zinc (168 mg) causing immediate decolorization of the solution. The colorless solution was stirred at room temperature for 2.5 h shielded from light. CH$_2$Cl$_2$ was added to the solution which was then filtered. The solvents were removed from the filtrate under reduced pressure. The crude material was purified by prep. TLC (20% ethyl acetate/hexane) to yield 29.5 mg of acridan 6i: $^1$H NMR (CDCl$_3$) δ 2.204 (s, 3H), 3.799 (s, 3H), 3.850 (s, 3H), 5.534 (s, 1H), 6.025 (s, 1H), 6.31–6.32 (d, 1H), 6.35–6.39 (d, 1H), 6.50–6.54 (dd, 1H), 6.80–7.03 (m, 3H), 7.42–7.45 (d 1H).

(f) The reduced product, acridan 6i (29.5 mg) was methylated with methyl trillate (0.5 mL) in 6 mL of CH$_2$Cl$_2$ under argon with protection from light. After 48 h, another 1 mL of methyl triflate was added and stirring continued for another day. The volatiles were evaporated and the product purified by prep. TLC using 20% ethyl acetate/hexane yielding 5i as a white solid: $^1$H NMR (CDCl$_3$) δ 2.373 (s, 3H), 3.478 (s, 3H), 3.838 (s, 3H), 3.876 (s, 3H), 5.447 (s, 1H), 6.53–6.64 (m, 3H), 6.77–7.01 (m, 2H), 7.07–7.10 (d, 1H), 7.30–7.34 (d, 1H).

Example 9

Synthesis of Compound 5i

2',3',6'-Trifluorophenyl 1,4,10-trimethylacridan-9-carboxylate.

(a) 2,5-Dimethylaniline (30 g, Aldrich) was converted to the acetamide derivative by reaction with 30.4 mL of acetic anhydride, 28.3 mL of acetic acid and 140 mg of zinc at reflux for 3 h. The reaction mixture was poured into 700 mL of ice water and stirred. The white solid was filtered, washed with water and air-dried yielding 24.88 g of the product: $^1$H NMR (CDCl$_3$) δ 1.561 (s, 3H), 2.221 (s, 3H), 2.322 (S, 3H), 6.88–6.92 (d, 1H) 7.05–7.09 (d, 1H), 7.61 (s, 1H).

(b) 2,5-Dimethylacetanilide (12.75 g) was condensed with 3-bromoanisole (25 mL) in the presence of 11.12 g of K$_2$CO$_3$ and 1.62 g of CuI at reflux for 4 d. After standing overnight, the mixture was heated and extracted with toluene (3×100 mL) and evaporated to a brown oil/solid mixture.

The oil was dissolved in 300 mL of ethanol, 8.77 g of KOH were added and the mixture refluxed for 24 h. The ethanol was evaporated and the oil taken up in 300 mL of water and extracted with CH$_2$Cl$_2$ (3×175 mL). The combined CH$_2$Cl$_2$ extracts were washed with water and purified by passing the solution through a plug of Na$_2$SO$_4$/silica/Na$_2$SO$_4$ which produced 10.25 g of the diphenylamine compound: $^1$H NMR (CDCl$_3$) δ 2.225 (s, 3H), 2.288 (s, 3H), 5.353 (s, 1H), 6.76–6.78 (d, 1H), 6.89–6.98 (m, 3H), 7.08–7.11 (d, 2H), 7.24–7.29 (t, 2H).

(c) Reaction of 2,5-dimethyldiphenylamine (10.25 g) with 5.21 mL of oxalyl chloride in 70 mL of CH$_2$Cl$_2$ at reflux for 45 min. followed by reaction with 13.86 g of AlCl$_3$ produced the isatin which was converted to 1,4-dimethylacridine-9-carboxylic acid (1j) (9.88 g) by base-catalyzed rearrangement with 125 mL of 10% KOH at reflux and neutralization with 500 mL of a 3:1 ice/5M HCl mixture: $^1$H NMR (DMSO-d$_6$) δ 2.80–2.82 (d, 6H), 7.40–7.42 (d, 1H), 7.63–7.66 (d, 1H), 7.70–7.75 (t, 1H), 7.90–7.93 (t, 1H), 7.96–7.99 (d, 1H), 8.21–8.24 (d, 1H) .

(d) Acid 1j (2.23 g) was suspended in excess SOCl$_2$ (35 mL) and the reaction mixture was heated until the acid dissolved and refluxed for another 30 min. The solvent was removed under reduced pressure and the acid chloride was combined with 2,3,6-trifluorophenol (0.69 g) and 15 mL of CH$_2$Cl$_2$. Pyridine (3.1 mL) was added dropwise under argon. The solution was stirred overnight at room temperature for about 4 days. The volatiles were removed under reduced pressure. The crude product was subjected to column chromatography on silica using 50% CH$_2$Cl$_2$/hexane to give 1.18 g of ester 3j: 1H NMR (CDCl$_3$) δ 2.881 (s, 3H), 2.930 (s, 3H), 7.09–7.31 (m, 2H), 7.35–7.37 (d, 1H), 7.56–7.58 (d, 1H), 7.65–7.72 (q, 1H), 7.80–7.86 (t, 1H), 8.23–8.27 (d, 1H), 8.32–8.35 (d, 1H).

(e) To a slurry of ester 3j (350 mg) and NH$_4$Cl (491 mg) in Ar-purged 2-propanol (20 mL) was added zinc (600 mg) causing immediate decolorization of the solution. The colorless solution was stirred at room temperature for 2 h shielded from light. CH$_2$Cl$_2$ was added to the solution which was filtered after 30 min. The solvents were removed from the filtrate under reduced pressure. The crude material was purified by column chromatography on silica using 5–10% ethyl acetate/hexane to yield 233 mg of acridan 6j: $^1$H NMR (CDCl$_3$) δ 2.290 (s, 3H), 2.420 (s, 3H), 5.504 (s, 1H), 6.141 (s, 1H), 6.73–7.01 (m, 6H), 7.20–7.23 (t, 1H), 7.46–7.48 (d, 1H).

(f) The reduced product, acridan 6j (233 mg) was methylated by stirring overnight with methyl triflate (5 mL) under argon with protection from light. The volatiles were evaporated and the product purified by column chromatography on silica using 15% ethyl acetate/hexane to yield 224 mg of 5j: $^1$H NMR (CDCl$_3$) δ 2.410 (s, 3H), 2.465 (s, 3H), 3.506 (s, 3H), 5.276 (s, 1H), 6.78–7.06 (m, 5H), 7.13–7.16 (d, 1H), 7.29–7.38 (m, 2H).

Example 10

Synthesis of Compound 5k

2',3',6'-Trifluorophenyl 1,4-dimethoxy-10-methylacridan-9-carboxylate.

(a) 2,5-Dimethoxyaniline (30 g, Aldrich) was converted to the acetamide derivative by reaction with 24 mL of acetic anhydride, 22.4 mL of acetic acid and 120 mg of zinc at reflux for 3 h. The reaction mixture was poured into 700 mL of ice-water and stirred. The purple solid was filtered, washed with 1 L of water and air-dried yielding 27.3 g of the product: $^1$H NMR (CDCl$_3$) δ 2.200 (s, 3H), 3.781 (s, 3H), 3.842 (s, 3H), 6.543–6.584 (dd, 1H), 6.77–6.80 (d, 1H), 7.77 (bs, 1H) 8.10–8.11 (d, 1H).

(b) 2,5-Dimethoxyacetanilide (12 g) was condensed with 3-bromoanisole (19.4 mL) in the presence of 8.75 g of K$_2$CO$_3$ and 1.27 g of CuI at reflux for 3 d. After standing overnight, the mixture was heated and then extracted with toluene (4×100 mL) and evaporated to a brown solid.

The solid was dissolved in 300 mL of ethanol, 6.9 g of KOH were added and the mixture refluxed for 48 h. The ethanol was evaporated and the crude product taken up in 300 mL of water and extracted with ethyl acetate (3×175 mL). The ethyl acetate extracts were combined, washed with water, dried over Na$_2$SO$_4$ and evaporated. The crude solid was purified by passing a CH$_2$Cl$_2$ solution through a short column containing layered Na$_2$SO$_4$/silica/Na$_2$SO$_4$ to produce 13.81 g of the diphenylamine compound: $^1$H NMR (CDCl$_3$) δ 3.750 (s, 3H), 3.864 (s, 3H), 6.210 (bs, 1H), 6.34–6.38 (dd, 1H), 6.79–6.82 (d, 1H), 6.92–7.00 (m, 2H), 7.18–7.20 (d, 2H), 7.28–7.33 (t, 2H).

(c) Reaction of 2,5-dimethoxydiphenylamine (5.0 g) with 2.19 mL of oxalyl chloride in 50 mL of CH$_2$Cl$_2$ and followed by reaction with 5.82 g of AlCl$_3$ in CH$_2$Cl$_2$ at reflux produced the isatin which was purified by flash chromatography on silica with CH$_2$Cl$_2$ yielding 2.2 g of the product as an orange solid: $^1$H NMR (CDCl$_3$) δ 3.756 (s, 3H), 3.799 (s, 3H), 6.59–6.62 (d, 1H), 6.88–6.89 (d, 1H), 6.98–7.05 (m, 2H), 7.11–7.16 (t, 1H), 7.48–7.53 (t, 1H), 7.66–7.69 (d, 1H).

(d) The isatin (3.55 g) was converted to 1,4-dimethoxy-acridine-9-carboxylic acid (1k) by refluxing with 30 mL of 10% KOH and neutralization with 3:1 ice/5M HCl yielding 3.4 g of acid 1k: $^1$H NMR (DMSO-d$_6$) δ 3.934 (s, 3H), 4.018 (s, 3H), 6.99–7.02 (d, 1H), 7.21–7.24 (d, 1H), 7.73–7.78 (t, 1H), 7.92–7.99 (m, 2H), 8.27–8.30 (d, 1H).

(e) Acid 1k (2.0 g) was suspended in excess SOCl$_2$ and the reaction mixture was heated until the acid dissolved. The solvent was removed under reduced pressure and the acid chloride was combined with 2,3,6-trifluorophenol (1.05 g) in CH$_2$Cl$_2$. Pyridine (2.5 mL) was added and the solution was stirred overnight at room temperature under argon. The volatiles were removed under reduced pressure. The crude product was subjected to column chromatography on silica using CH$_2$Cl$_2$ to give 0.44 g of ester 3k: $^1$H NMR (CDCl$_3$) δ 4.007 (s, 3H), 4.143 (s, 3H), 6.81–6.84 (d, 1H), 7.00–7.22 (m, 3H), 7.68–7.73 (dt, 1H), 7.83–7.89 (dt, 1H), 8.23–8.26 (d, 1H), 8.45–8.48 (d, 1H).

(f) To a slurry of ester 3k (440 mg) and NH$_4$Cl (569 mg) in Ar-purged 2-propanol (15 mL) was added zinc (696 mg) causing immediate decolorization of the solution. The colorless solution was stirred at room temperature for 2.5 h shielded from light. CH$_2$Cl$_2$ was added to the solution which was then filtered. The solvents were removed from the filtrate under reduced pressure. The crude material was again extracted with CH$_2$Cl$_2$ and the filtrate evaporated. The product was purified by column chromatography using 2.5–20% ethyl acetate/hexane to yield 272 mg of acridan 6i: $^1$H NMR (CDCl$_3$) δ 3.836 (s, 3H), 3.874 (s, 3H), 5.601 (s, 1H), 6.31–6.34 (d, 1H), 6.68–7.01 (m, 6H), 7.17–7.22 (t, 1H), 7.51–7.54 (d, 1H).

(g) The reduced product, acridan 6k (272 mg) was methylated with methyl triflate (0.74 mL) in 5 mL of CH$_2$Cl$_2$ under argon with protection from light. After 3 d the volatiles were evaporated and the product purified by column chromatography using 5% ethyl acetate/hexane yielding 200 mg of 5k: $^1$H NMR (CDCl$_3$) δ 3.581 (s, 3H), 3.817 (s, 3H), 3.866 (s, 3H), 5.547 (s, 1H), 6.50–6.53 (s, 1H), 6.77–7.01 (m, 4H), 7.08–7.11 (d, 1H), 7.27–7.33 (m, 1H), 7.40–7.43 (d, 1H).

Chemiluminescence Measurements

The experiments in the following examples were performed using either a Turner Designs TD-20e (Sunnyvale, Calif.) luminometer fitted with neutral density filter for light attenuation or a Labsystems Luminoskan (Helsinki, Finland) luminometer. Data collection, analysis and display were software controlled.

Example 11

A detection reagent was prepared by combining in a 40:1 ratio reagent A consisting of: 0.6 mM urea peroxide, 0.1 mM p-phenylphenol, 0.025% TWEEN 20, 1 mM EDTA in 0.01M tris buffer, pH 8.0 and reagent B consisting of: acridan 5c (0.86 mg/mL) in 1:1 (v/v) p-dioxane/ethanol or 1:1 (v/v) propylene glycol/ethanol. To 40 µL of the resulting solution, 1 µL of HRP ((1.4×10$^{-16}$ mol)) was added and the solution incubated for 5 min. A flash of luminescence was induced by injecting 100 µL of 0.1M NaOH solution. A blank was performed by repeating the experiment without the addition of enzyme. FIG. 1 shows the generation of light emission which resulted.

Example 12

An experiment according to Example 11 was repeated using a detection reagent prepared by combining reagents A and B in a 1200:1 ratio and an incubation time of 100 sec. A better signal/background ratio resulted due to a lowering of the light intensity of the blank.

Example 13

Figure 2:
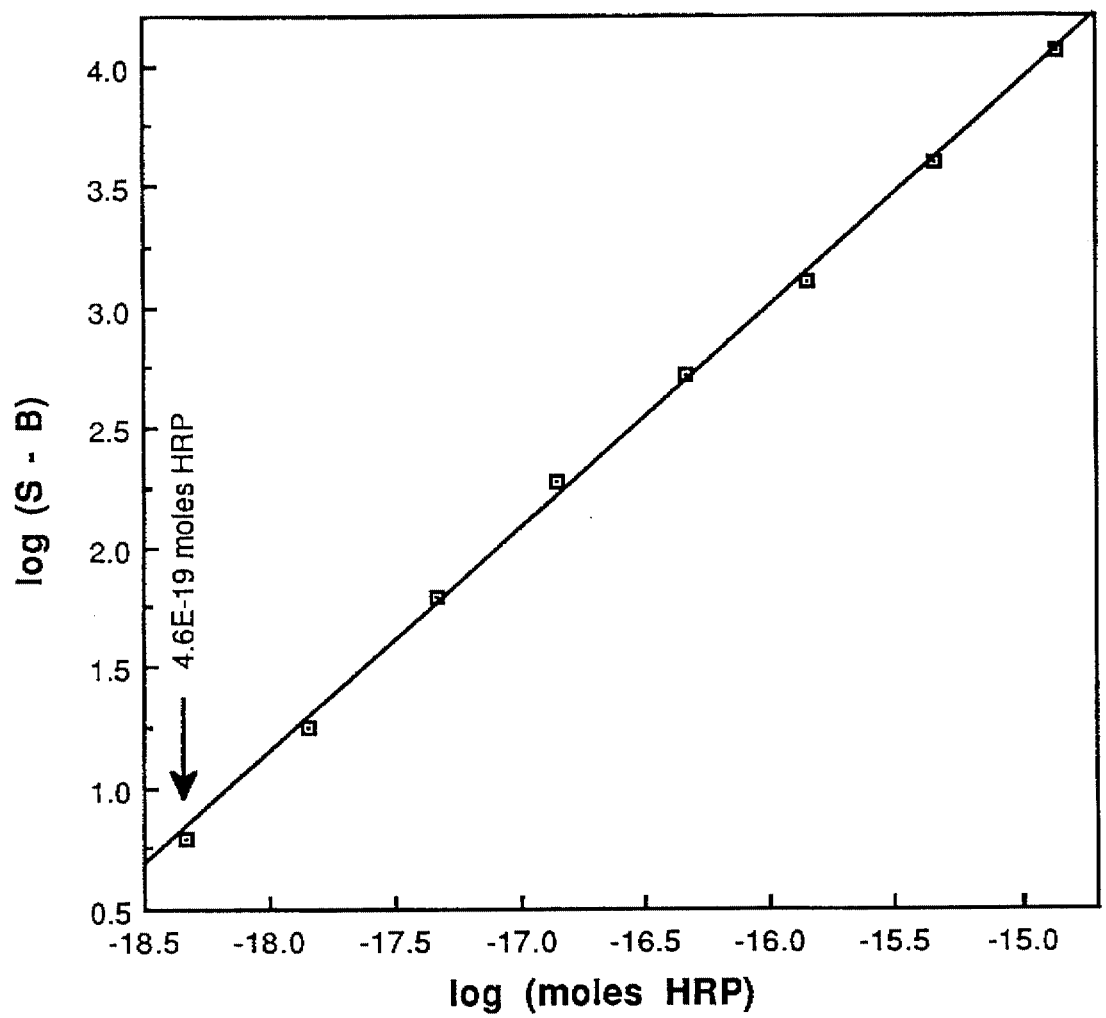

The sensitivity and linearity of detection of HRP using the detection reagent of Example 12 was determined. In each of 3 wells of a microplate, 50 µL volumes of the detection reagent were mixed at room temperature with 1 µL aliquots of solutions of HRP containing between 1.4×10$^{-15}$ and 1.4×10$^{-19}$ mol of enzyme. After 100 sec, 100 µL of 0.1M NaOH was added and luminescence integrated for 2 sec. FIG. 2 shows the linear range of HRP amount measured using a reagent of the present invention containing acridan 5c.

Example 14

A detection reagent according to the composition of Example 11 containing instead the acridan 5b was tested for detection of HRP. The method specified in example 10 was followed with the exception that the detection solution was incubated with the enzyme for 5 min. The lowest detected amount of HRP was 1.4 amol (1.4×10$^{-18}$ mol) with a signal/background ratio of 2.

Example 15

A detection reagent according to the composition of Example 11 containing instead a slightly impure preparation of the acridan 5d was tested for detection of HRP. Following the method specified in example 10, 1.4×10$^{-6}$ mol of HRP incubated with the reagent and flashed with NaOH produced a signal 105 times greater than the blank. Using 1.4×10$^{-17}$ mol of HRP and incubating for 10 min produced a signal 69 times greater than the blank. The principal impurity, the N-demethylated analog (6d) was tested independently under the conditions of the experiment and found not to produce a significant amount of light.

Example 16

A detection reagent according to the composition of Example 11 containing instead a crude preparation of the acridan 5h was tested for detection of HRP. Following the method specified in example 10, $1.4 \times 10^{-16}$ mol of HRP incubated with the reagent for 3 min and treated with 0.1M NaOH produced a signal 72 times greater than the blank. The principal impurity, the N-demethylated analog (6h) was tested independently under the conditions of the experiment and found not to produce light.

Example 17

Effect of Enhancers

Detection reagent solutions according to the composition of Example 11 may be prepared with substitution of various phenolic enhancers, reacted with HRP and subsequently made highly basic. Useful levels of light intensity compared to reagent background are obtained with reagents incorporating p-iodophenol, p-bromophenol, p-hydroxycinnamic acid, 2-naphthol, 6-bromo-2-naphthol and 4-iodophenylboronic acid.

Example 18

Effect of Peroxide

Detection reagent solutions according to the compositions of Example 11 may be prepared with substitution of various peroxides, reacted with HRP and subsequently made highly basic. Useful levels of light intensity compared to reagent background are obtained with reagents incorporating hydrogen peroxide, sodium perborate and urea peroxide.

Example 19

Figure 3:
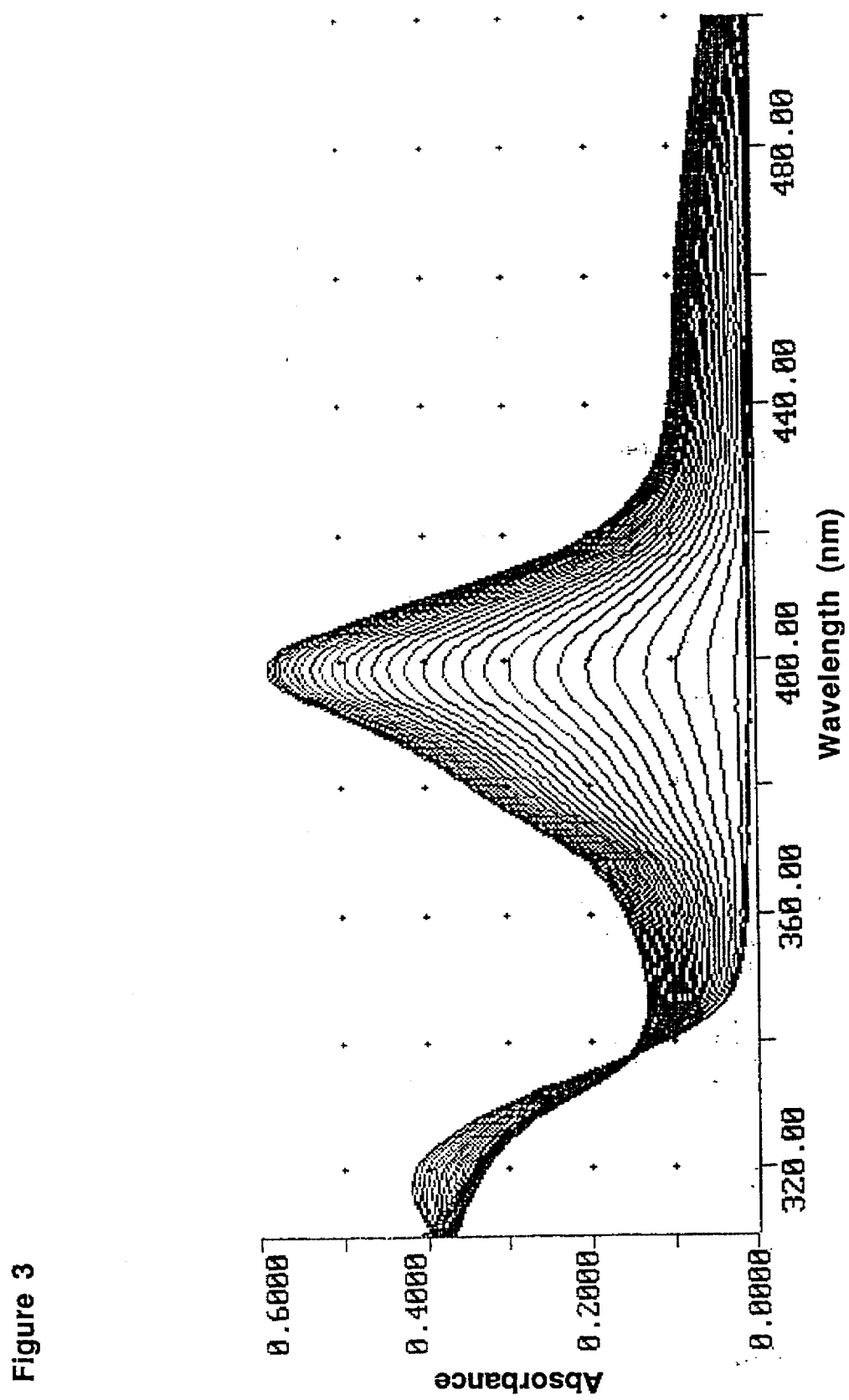

A solution of the reagent of Example 11 containing acridan 5c (3 mL) was placed in a quartz cuvette in a Varian Cary 3E (Palo Alto, Calif.) UV-Vis spectrophotometer. HRP ($1.4 \times 10^{-15}$ mol) was added and the absorbance spectrum between 300–500 nm scanned at 30 sec intervals. FIG. 3 shows the formation (in the direction bottom curve to top curve at 400 nm) of the acridinium compound 4c. After 15 min no further change was observed in the spectrum. A 0.1M NaOH solution was added causing a burst of blue light. The spectrum of the resulting solution matched the absorption of 1,6-dimethoxy-10-methylacridone.

Example 20

Figure 4:
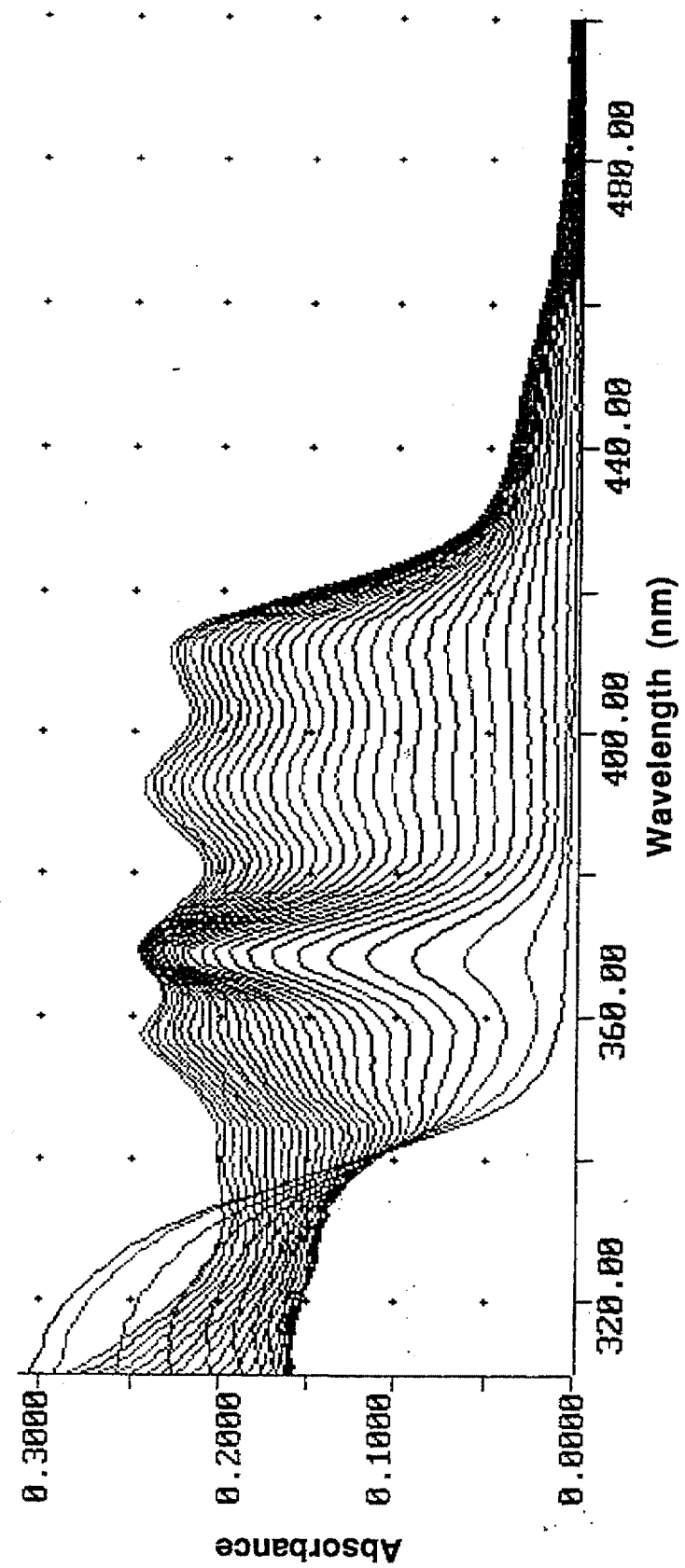

To demonstrate that acridans bearing alkyl, alkoxy and/or halogen substituents on the acridan ring provide superior performance to similar acridans which are unsubstituted on the acridan ring, the experiment of Example 20 was repeated using an acridan compound which is unsubstituted on the acridan ring. A solution of a reagent similar to that used in Example 11 (3 mL) but containing the acridan 2',6'-difluorophenyl 10-methylacridan-9-carboxylate was reacted with HRP ($1.4 \times 10^{-15}$ mol) and the absorbance spectrum between 300–500 nm scanned at 30 sec intervals. FIG. 4 shows the formation (in the direction bottom curve to top curve at 400 nm) of both the acridinium compound 2',6'-difluorophenyl 10-methylacridinium-9-carboxylate and N-methylacridone as proven by comparison with authentic samples of these two compounds. In addition, subjecting the acridinium compound 2',6'-difluorophenyl 10-methylacridinium-9-carboxylate to the same reagent formulation in the absence of added HRP led to measurable conversion to the same acridone within minutes.

Example 21

The sensitivity and linearity of detection of HRP using the detection reagent containing acridan 5i was determined. The reagent contained acridan 5i (0.05 mM) (diluted 1:40 from a 2 mM stock solution in 1:1 ethanol/p-dioxane), 0.1 mM p-phenylphenol, 0.025% TWEEN 20, 0.5 mM urea peroxide and 1 mM EDTA in 0.01M tris buffer, pH 8.0. In each of 3 wells of a microplate, 100 µL volumes of the detection reagent were mixed at room temperature with 10 µL aliquots of solutions of HRP containing between $1.4 \times 10^{-15}$ and $1.4 \times 10^{-19}$ mol of enzyme or 10 µL of water as a reagent blank. After 5 min, 100 µL of 0.1M NaOH was added and the total luminescence integrated for 2 sec. Light emission was proportional to the amount of HRP with a calculated detection limit $<10^{-18}$ mol.

Example 22

The sensitivity and linearity of detection of HRP using the detection reagent containing acridan 5j was determined. The reagent contained acridan 5j (0.05 mM) (diluted 1:40 from a 2 mM stock solution in 1:1 ethanol/p-dioxane), 0.1 mM p-phenylphenol, 0.025% TWEEN 20, 0.5 mM urea peroxide and 1 mM EDTA in 0.01M tris buffer, pH 8.0. In each of 3 wells of a microplate, 100 µL volumes of the detection reagent were mixed at room temperature with 10 µL aliquots of solutions of HRP containing between $1.4 \times 10^{-15}$ and $1.4 \times 10^{-19}$ mol of enzyme or 10 µL of water as a reagent blank. After 5 min, 100 µL of 0.1M NaOH was added and the total luminescence integrated for 2 sec. Light emission was proportional to the amount of HRP with a calculated detection limit of $1.4 \times 10^{-19}$ mol. Similar results were obtained in another set of experiments in which the flash reagent consisted of 0.1M NaOH and 0.1 mM SDS and peak light intensity was measured instead of total intensity.

Example 23

The sensitivity and linearity of detection of HRP using the detection reagent containing acridan 5k was determined. The reagent contained acridan 5k (0.05 mM) (diluted 1:40 from a 2 mM stock solution in 1:1 ethanol/p-dioxane), 0.1 mM p-phenylphenol, 0.025% TWEEN 20, 0.5 mM urea peroxide and 1 mM EDTA in 0.01M tris buffer, pH 8.0. In each of 3 wells of a microplate, 100 µL volumes of the detection reagent were mixed at room temperature with 10 µL aliquots of solutions of HRP containing between $1.4 \times 10^{-15}$ and $1.4 \times 10^{-19}$ mol of enzyme or 10 µL of water as a reagent blank. After 5 min, 100 µL of 0.1M NaOH was added and the maximum luminescence intensity was measured. Light intensity was proportional to the amount of HRP with a calculated detection limit $<10^{-18}$ mol.

It is intended that the foregoing description be only illustrative of the present invention and that the present invention be limited only by the appended claims.

We claim:

1. A compound which is 2',3',6'-trifluorophenyl 1,6-dimethoxy-10-methylacridan-9-carboxylate.

2. A compound which is 2',3',6'-trifluorophenyl 4-chloro-3-methoxy-10-methylacridan-9-carboxylate.

3. A compound which is 4'-fluorophenyl 4-chloro-3-methoxy-10-methylacridan-9-thiocarboxylate.

4. A compound which is 2',3',6'-trifluorophenyl-1,4-dimethoxy-10-methylacridan-9-carboxylate.

5. A compound which is 2',3',6'-trifluorophenyl 1,4,10-trimethylacridan-9-carboxylate.

6. A compound which is 2',3',6'-trifluorophenyl 1,6-dimethoxy-4,10-dimethylacridan-9-thiocarboxylate.

7. A compound having the formula:

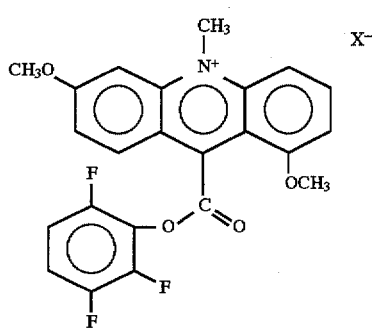

wherein X is an anion.

8. A compound having the formula:

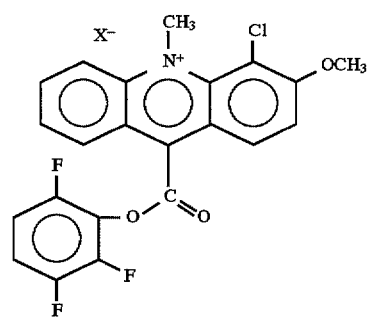

wherein X is an anion.

9. A compound having the formula:

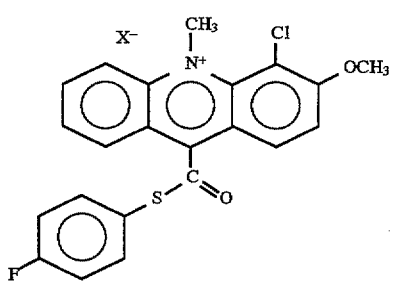

wherein X is an anion.

10. A compound having the formula:

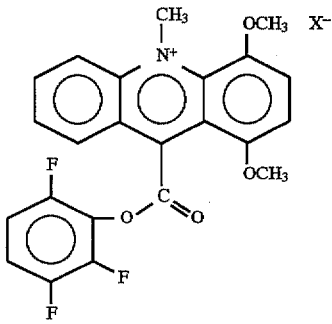

wherein X is an anion.

11. A compound having the formula:

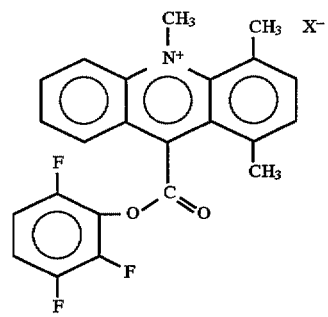

wherein X is an anion.

12. A compound having the formula:

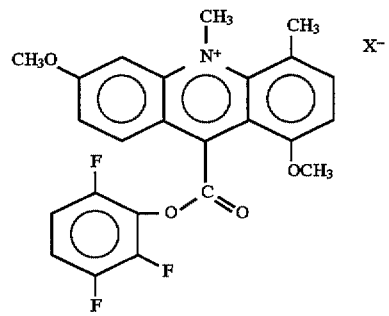

wherein X is an anion.

* * * * *

UNITED STATES PATENT AND TRADEMARK OFFICE
CERTIFICATE OF CORRECTION

PATENT NO. : 5,670,644

DATED : September 23, 1997

INVENTOR(S) : H. Akhavan-Tafti, et al

It is certified that error appears in the above-indentified patent and that said Letters Patent is hereby corrected as shown below:

Column 5, line 53, "RNAby" should read --RNA by--

Column 6, line 43, "phenoxyand" should read --phenoxy and--

Column 16, line 21, "3.84 (S,3H), 3.90 (S, 3H)" should read --3.84 (s,3H), 3.90 (s, 3H)--

Column 16, line 29, "isolatedby" should read --isolated by--

Column 16, line 36, "1H NMR" should read --$^1$H NMR--

Column 17, line 3, "retool" should read --mmol--

Column 17, line 30, "4 g" should read --4.0 g--

Column 18, line 36, "5 h" should read --5h--

Column 18, line 36, "3.441 (S, 3H)" should read --3.441 (s, 3H)--

Column 19, line 42, "trillate" should read --triflate--

Column 19, line 53, "Synthesis of Compound 5i" should read --Synthesis of Compound 5j--

UNITED STATES PATENT AND TRADEMARK OFFICE
CERTIFICATE OF CORRECTION

PATENT NO. : 5,670,644

DATED : September 23, 1997

INVENTOR(S) : H. Akhavan-Tafti, et al

It is certified that error appears in the above-indentified patent and that said Letters Patent is hereby corrected as shown below:

Column 19, line 63, "2,322 (S, 3H)" should read --2.322 (s, 3H)--

Signed and Sealed this

Twenty-third Day of June, 1998

Attest:

BRUCE LEHMAN

Attesting Officer

Commissioner of Patents and Trademarks